United States Patent [19]

Curtis

[11] Patent Number: 5,514,119

[45] Date of Patent: May 7, 1996

[54] EMBRYO COLLECTION DEVICE

[76] Inventor: John L. Curtis, P.O. Box 1222, Manhattan, Kans. 66502

[21] Appl. No.: 293,075

[22] Filed: Aug. 19, 1994

[51] Int. Cl.[6] .................................................. A61M 1/00
[52] U.S. Cl. .......................... 604/319; 604/317; 128/760
[58] Field of Search .................................. 128/760, 771; 604/317–319

[56] References Cited

U.S. PATENT DOCUMENTS

| | | |
|---|---|---|
| 354,384 | 12/1886 | Bovey . |
| 1,605,887 | 11/1926 | Banks . |
| 1,918,351 | 7/1933 | Schulze . |
| 2,675,000 | 4/1954 | Ford . |
| 2,742,849 | 4/1956 | Stiglitz . |
| 3,769,171 | 10/1973 | Grimes et al. . |
| 3,773,211 | 11/1973 | Bridgman . |
| 4,071,027 | 1/1978 | Meador . |
| 4,275,731 | 6/1981 | Nichols . |
| 4,275,732 | 6/1981 | Gereg . |
| 4,516,973 | 5/1985 | Telang . |
| 4,563,172 | 1/1986 | Ferguson . |
| 4,781,706 | 11/1988 | Suzuki et al. . |
| 4,809,860 | 3/1989 | Allen . |
| 4,957,492 | 9/1990 | McVay . |
| 5,042,979 | 8/1991 | Anderson et al. . |
| 5,223,151 | 6/1993 | Rojas ....................................... 210/767 |
| 5,252,222 | 10/1993 | Matkovich et al. ..................... 210/650 |
| 5,301,685 | 4/1994 | Guirquis ................................. 128/760 |

FOREIGN PATENT DOCUMENTS

| | | |
|---|---|---|
| 051988A1 | 4/1992 | European Pat. Off. . |
| 1590070A1 | 11/1988 | U.S.S.R. . |
| 1655486A | 4/1989 | U.S.S.R. . |
| 1704775A1 | 3/1990 | U.S.S.R. . |
| 2070437 | 2/1980 | United Kingdom . |

*Primary Examiner*—Randall L. Green
*Assistant Examiner*—Mark O. Polutta
*Attorney, Agent, or Firm*—Hovey, Williams, Timmons & Collins

[57] ABSTRACT

An improved embryo collection device (10) is provided which minimizes the possibility of embryo damage or loss while facilitating rapid collection, isolation and extraction of embryos from an embryo-containing irrigant fluid. The device (10) includes a vessel (12) including an outlet port (22) for conveying filtered irrigant fluid out of vessel (12), a filter insert (14) positioned within vessel (12) for filtering embryos out of the irrigant fluid, and a lid (16) removably connected to the filter insert (14) including an inlet port (50) for delivering embryo-containing irrigant fluid to the vessel (12). The vessel (12) is formed of light-transmitting translucent or transparent material, and the filter insert (14) preferably includes isolation cells (42) so that the collection device (10) can be directly placed within a microscope for rapid examination and extraction of collected embryos (91). The outlet port (22) is spaced a distance above the base (18) and filter (26) to allow retention of a minimum level of fluid within the device (10) to prevent embryos from drying out during collection and examination. The inlet port (50) is oriented for directing incoming irrigant fluid to the filter insert (14) at a fluid level at least slightly below the minimum fluid level in vessel (12). Thus, incoming irrigant fluid does not cause splashing or foam formation.

12 Claims, 1 Drawing Sheet

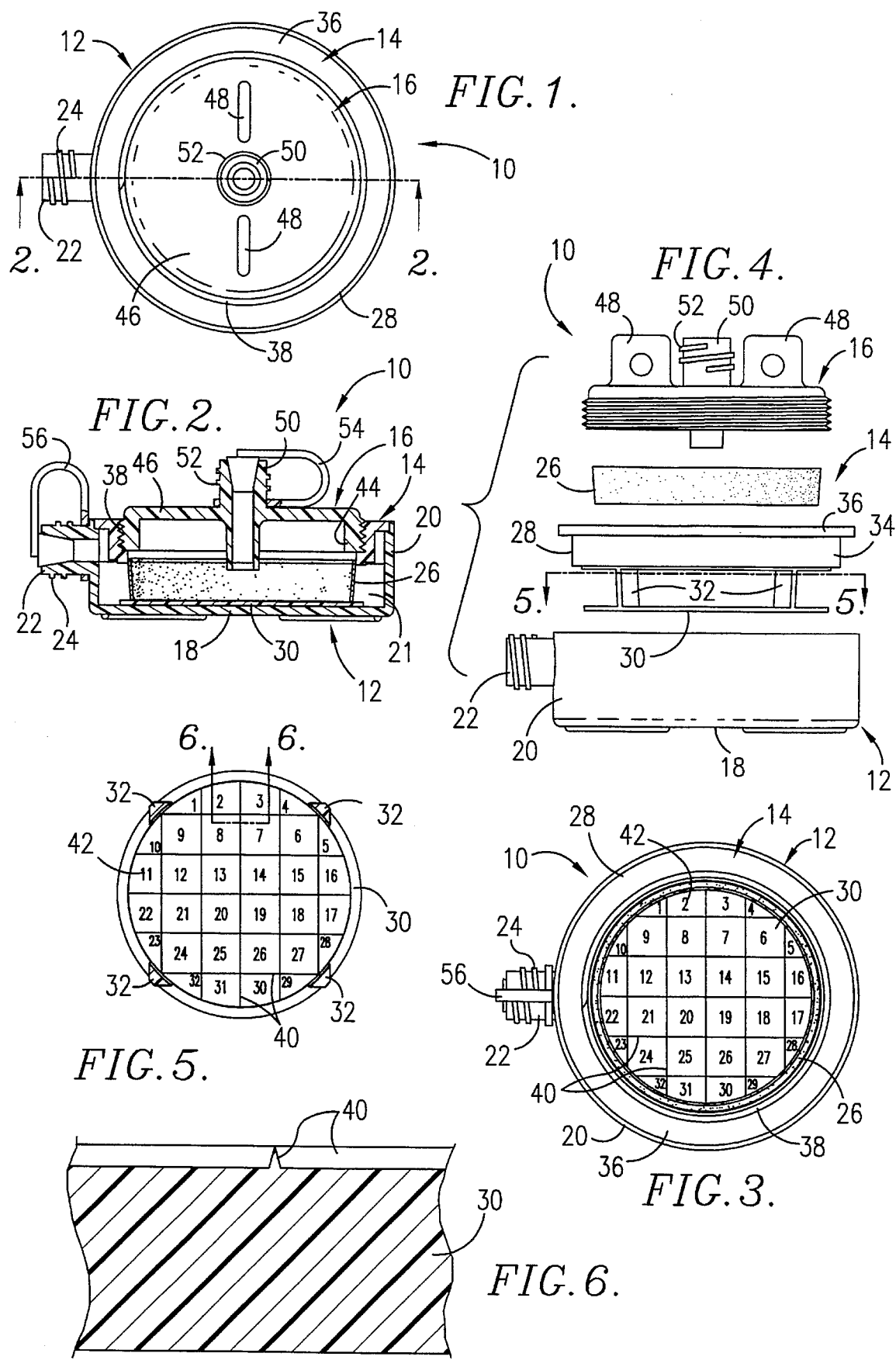

5,514,119

EMBRYO COLLECTION DEVICE

BACKGROUND OF THE INVENTION

1. Field of the Invention

The present invention is broadly concerned with an improved embryo collection device of the type used for extracting and identifying mammalian embryos from an embryo-containing irrigant fluid. More particularly, it is concerned with such an embryo collection device which in preferred forms includes an outer vessel provided with a light-transmitting base permitting the collection device to be situated within a microscope in order to allow direct identification and counting of extracted embryos without the need for transfer of such embryos to a counting dish. The outer vessel advantageously includes an outlet port spaced a distance above the bottom wall for conveying filtered irrigant fluid from the vessel device while allowing retention of sufficient fluid within the collection device to prevent the filter and collected embryos from drying out. A specialized fluid inlet nipple is also provided which discharges incoming irrigant fluid at a level below the minimum fluid level maintained within the vessel, thereby avoiding splashing and formation of foam.

2. Description of the Prior Art

Mammalian (e.g., bovine) embryos are routinely removed from female donor animals by a process which involves flushing of the donor animal uterus with an irrigant fluid. The embryo-containing irrigant fluid is then collected, and steps are taken to extract the embryos from the relatively large volume of collected irrigant fluid. It has been known in the past to collect embryo-containing fluid in a container, while attempting to keep the irrigant fluid moving. As a part of this procedure, the irrigant was decanted or otherwise drained from the container, and the embryos were then transferred to a petri or other counting dish for examination. This approach is inherently time-consuming and necessitates handling of the embryos between the settling container and the counting dish.

U.S. Pat. No. 4,563,172 describes an embryo collection device having an intermediate collection chamber equipped with a filter, together with an upper cover member provided with an irrigant fluid inlet, and a funnel-shaped receipt chamber beneath the filter with a discharge aperture at the bottom of the receipt chamber. One significant problem with this collection device is that the irrigant fluid inlet directs the incoming fluid vertically downwardly in an unimpeded fashion for a substantial free-fall distance within the device. This inevitably creates a foamy "head" on the fluid within the device due to the serum component in the irrigant, which often requires aspiration of the head in order to permit visualization of the microscopic ova which are easily obscured by the foamy bubbles. The aspirated head must be retained and carefully inspected though, inasmuch as valuable embryos can be carried over in this fraction.

The presence of foam in the search dish is undesirable since it obscures vision and therefore greatly slows the microscope search process. Embryos also stick to bubbles and at that point are very difficult to locate and extract. Most technicians aspirate the foam head off with a syringe immediately prior to searching and do not wait 10–20 minutes for the foam head to dissolve. The drawback to aspiration is that embryos attached to bubbles will unknowingly be removed in the syringe!

As described in the '172 patent, in the use of the collection device it is important to maintain a level of fluid in the collection chamber sufficient to keep the embryos in suspension and prevent the embryos from settling against the filter; otherwise, the embryos may be unacceptably damaged. This mode of operation is also necessitated by virtue of the straight-through vertical design of the irrigant fluid inlet and the consequent likelihood of embryo damage if an insufficient volume of fluid is present in the device. Moreover, inasmuch as the patented collection device includes a funnel-shaped receipt chamber beneath the filter, it is necessary to transfer the collected embryos to a separate counting dish for detailed examination, and this constitutes another undesirable handling step.

If, contrary to the teachings of the '172 patent, collected embryos actually settle out or otherwise come into contact with the filter, the device must be repeatedly rinsed and swirled in an effort to resuspend all of the embryos for transfer examination and counting. This problem is particularly acute given the foaming tendency of the irrigant fluid and because the fluid includes uterine endometrial and mucous membrane debris which can entrap embryos. Therefore, it is often very difficult to insure that all embryos are properly transferred when using the device of the '172 patent.

A more recent embryo collection device is described in U.S. Pat. No. 4,781,706, which illustrates a vessel with a bottom wall and an upstanding sidewall presenting a filter opening above the bottom wall; an embryo filter is attached to the sidewall opening. A cover member having an irrigant fluid inlet is also provided, which permits incoming embryo-containing fluid to be passed into the vessel for filtration. As with the '172 patent, the irrigant fluid inlet directs the incoming fluid vertically downwardly in an unimpeded fashion for a substantial free-fall distance within the device, creating a foamy "head" as described above. Another significant problem with the collection device provided by the '706 patent is that after filtration is complete, only a low level of irrigant fluid remains within the vessel, this level being dictated by the height of the filter above the vessel bottom wall. As a consequence, however, the filter itself necessarily dries out because it is no longer exposed to irrigant fluid after filtration. This in turn means that valuable embryos can adhere to the filter, dry out and be lost.

Prior art embryo collection devices suffer from a number of other limitations. For example, entrance ports to prior art devices are straight male ports which require the user to wedge the end of the Y-junction tubing over and down the shaft, which can be difficult to accomplish on a cold day when the tubing is stiff. Another drawback to this prior art design is that after the embryos are collected, the user must separate the tubing from the device in order to transport the device to the microscope. This separation is accomplished by either pulling, twisting, or stretching the tubing until the friction is overcome. As a result, the tubing often pops loose suddenly from the nipple and violently jars the device and embryos therein. Or, one must take scissors and cut the tubing to separate it from the device.

Lastly, this attachment method is not as secure as one would like since in cold weather the tubing friction hold on the nipple is reduced since tubing pliability and "stickiness" is reduced in cold temperatures.

Another limitation of prior art collection devices is that they have lids which are connected to their lower collection vessels by a snap-on or friction attachment arrangement. Friction attachment is adequate if the practitioner has an assistant to hold the filter with "kid gloves" and the device is never dropped, bumped, or left to hang suspended by tubing over a bar on the cattle squeeze chute. However, all of the above situations occur routinely and therefore many practitioners use rubber bands to secure the lid to the base, or ask someone to hold the filter throughout the collection period. The lid is even more likely to disconnect from the base in cold weather. Cold weather causes frequent problems because most dairy and beef cattle are collected year-round, most exclusively on-farm in the barn.

All known self-draining, direct-examination devices are also plagued with the problem of leaking fluid onto the microscope stage. This occurs as the dish is moved up, down, and back and forth across the scope stage during the search process which causes fluid to splash either against or through the filter and onto the stage. To avoid this design flaw, the user must take a syringe and aspirate a substantial amount of fluid out of this "micro-pool" prior to placing the vessel onto the stage. Unfortunately, syringe aspiration in this limited fluid depth can unknowingly draw embryos up into the syringe.

The standard petri dish used most exclusively today for embryo isolation/extraction has several handicaps. In the standard petri dish, embryos sink in the fluid and come to rest on top of the horizontal bottom wall of the dish. As the technician moves the dish in an "S" pattern over the microscope stage during the search process, embryos roll and change location in the dish. Even when a gridded pattern is etched on the bottom, embryos roll around (shift position) in the bottom of the dish due to the fluid wave motion inevitably caused by dish movement over or across the scope stage.

SUMMARY OF THE INVENTION

The present invention overcomes the problems outlined above and provides a greatly improved embryo collection device which not only reduces the time required for embryo collection and identification, but also greatly minimizes embryo loss and damage due to improper embryo retrieval and handling. The preferred embryo collection device broadly includes a vessel with an outlet port for conveying filtered fluid out of the device, a filter insert located within the vessel, and a lid removably connected to the filter insert including an inlet port for delivering embryo-containing irrigant fluid to the filter insert.

More particularly, the vessel has a planar bottom wall and an upstanding sidewall. The walls define a vessel for retaining filtered fluid therein, and the sidewall includes an outlet port for conveying filtered irrigant fluid from the vessel during use thereof. The outlet port is spaced a distance above the vessel bottom wall to allow retention of sufficient fluid within the vessel to prevent the embryos from drying out during collection and examination while also permitting easy insertion of hand-held or mechanical catheters for specimen manipulation and removal.

The filter insert is contained within the vessel and includes an upright filter spaced inwardly from the vessel sidewall, thereby presenting an irrigant fluid-retaining region between the upright filter and the vessel sidewall. The filter insert retains embryos for examination and delivers the filtered fluid to the outboard region and then out the outlet port. The upright filter is advantageously positioned with the upper margin thereof below or at least generally at the level of the vessel outlet port so that the filter is substantially completely immersed in fluid during and subsequent to filtration operations. Thus, embryos which may adhere to the filter during the filtration sequence remain hydrated and recoverable.

The lid member is removably and securely attached to the filter insert by a unique threaded attachment arrangement which provides a leak-proof seal with the vessel. Lid member includes an irrigant fluid inlet for delivering embryo-containing irrigant fluid to the filter insert. The inlet is advantageously oriented for directing incoming irrigant fluid to the filter insert at a fluid level at least slightly below the minimum fluid level existing in the vessel by virtue of the location of the outlet port. In this way, incoming irrigant fluid does not cause splashing and subsequent foaming with the existing irrigant fluid contained in the vessel. To provide a leak-proof seal with incoming fluid, the inlet and outlet parts are threaded to allow connecting tubing to be attached quickly and securely.

The vessel base is generally translucent for permitting the entire device to be situated within a microscope in order to allow direct identification and counting of extracted embryos without the need for transfer of such embryos to a counting dish. Finally, the preferred filter insert includes a series of discrete isolation cells, thereby further facilitating embryo identification and extraction. Accordingly, the conventional step of transferring embryos from a collection device to a counting dish is completely eliminated.

BRIEF DESCRIPTION OF THE DRAWINGS

FIG. 1 is a plan view of an embryo collection device in accordance with the invention;

FIG. 2 is a vertical sectional elevational view taken along line 2—2 of FIG. 1;

FIG. 3 is a plan view of the collection device shown with the lid thereof removed;

FIG. 4 is an exploded view of the preferred embryo collection device;

FIG. 5 is a sectional view taken along line 5—5 of FIG. 4 depicting the underlying grid structure and posts of the filter insert; and FIG. 6 is a sectional view taken along line 6—6 of FIG. 5 illustrating the construction of the grid structure.

DETAILED DESCRIPTION OF THE PREFERRED EMBODIMENTS

Turning to the drawings, and particularly FIG. 4, an embryo collection device 10 is depicted. The preferred collection device 10 broadly includes a vessel 12, a filter insert 14, and a lid member 16. As described in detail below, vessel 12, filter insert 14, and lid 16 cooperate for extracting and holding embryos from an incoming, embryo-containing irrigant fluid so that the extracted embryos can be removed or observed in the collection device under a microscope.

In more detail, vessel 12 is essentially cup-shaped and includes a planar, circular base 18 and an upright, vertically extending, continuous sidewall 20. Base 18 and sidewall 20 define an open vessel 21 for receiving filter insert 14 and for retaining irrigant fluid therein. Base 18 and sidewall 20 are preferably formed of transparent synthetic resin material and are at least translucent for passage of light therethrough. Vessel 12 and lid 16 have a sufficiently low profile for allowing the device 10 to be used in a microscope, thereby permitting identification and counting of embryos extracted from the irrigant fluid without need for transfer of the extracted embryos.

As best illustrated in FIGS. 1 and 4, sidewall 20 includes a tubular outlet port 22 for conveying filtered irrigant fluid from the vessel 12. The preferred outlet port 22 is a conventional horizontally-extending, tapered, tubular fluid outlet nipple and includes outwardly extending threads 24. Outlet port 22 is adapted to mate with a conventional flexible discharge conduit (not shown). The threaded design of outlet port 22 facilitates easy attachment and removal of the discharge conduit. As illustrated in FIG. 4, outlet port 22 is advantageously spaced a distance above base 18 to allow retention of a minimum fluid level within the vessel 12 to prevent the embryos from drying out during collection and examination, while also permitting easy insertion of hand-held or mechanical catheters for specimen manipulation and removal.

As illustrated in FIG. 4, filter insert 14 broadly includes an upright filter 26 and a filter support structure 28. Filter insert 14 is contained within vessel 12 and is configured for filtering embryos from embryo-containing fluid delivered thereto.

In more detail, filter 26 is essentially circular in plan configuration and is preferably made of a woven nylon mesh material. The openings in the mesh are sized so that filter 26 is permeable to liquid but prevents passage of embryos therethrough.

Support structure 28 supports filter 26 in vessel 12 and includes a bottom wall 30, a plurality of upstanding support posts 32, and an annular connector wall 34. Bottom wall 30 is circular in configuration and is bonded to the inner surface of base 18. Support posts 32 are circumferentially spaced and integrally molded to bottom wall 30 and extend upwardly therefrom. Connector wall 34 is an upright, vertically extending, continuous wall supported at the upper ends of posts 32. Connector wall 34 includes an integral, outwardly extending, continuous horizontal flange 36 for engaging the top of vessel sidewall 20. As best illustrated in FIG. 2, connector wall 34 further includes integral internal threads 38 for engaging threaded lid member 16 as described below.

As best illustrated in FIG. 2., filter 26 and filter support structure 28 are contained within vessel 12, with the filter 26 being spaced inboard of vessel sidewall 20. Accordingly, an annular fluid-retention region is defined between the outer face of filter 26 and the inner surface of sidewall 20. Support structure 28 supports filter 26 so that the filter bottom edge engages bottom wall 30 and the upper margin of the filter engages connector wall 34. In this way, embryo-containing irrigant fluid is first delivered to the central region of insert 14 and thence moves laterally through the filter 26 for passage into the described region and ultimately out port 22. During this operation, the filter 26 filters embryos from the irrigant fluid and causes them to descend to bottom wall 30 into isolation cells for later inspection.

In preferred forms, the upper margin filter 26 is positioned at or slightly below the outlet port 22 so that the filter 26 is completely immersed in fluid when the embryo collection device is in use. Thus, embryos which adhere to the filter during filtration remain hydrated and embryo loss and damage due to dehydration is eliminated.

As illustrated in FIGS. 3, 5 and 6, bottom wall 30 includes a plurality of upwardly extending, intersecting ribs 40 defining isolation cells 42 which serve to isolate and localize embryos. Isolation cells 42 eliminate embryo drift which occurs when vessel 12 is moved across the microscope stage during the search process. Isolation cells 42 may also include numbers or other indicia imprinted thereon for creating a series of discrete locator cells, thereby further facilitating the search process.

As best illustrated in FIG. 4, lid member 16 is removably attached to filter insert 14 for sealing the open vessel 12. Lid member 16 broadly includes an annular sidewall 44 and a circular top wall 46. The outside diameter of sidewall 44 is slightly smaller than the inside diameter of connector wall 34 and is threaded for engaging the threads of filter support structure 28. In this way, lid 16 is securely attached to vessel 12 and provides a leak-proof seal which will not open unexpectedly.

Top wall 46 includes a pair of upstanding handles 48 to facilitate screwing and unscrewing of lid 16. Handles 48 also serve as an attachment point for tethering the device to the user, donor, or cattle squeeze chute during use, thereby eliminating the need for an assistant to hold the device.

Lid member top wall 46 includes structure defining an irrigant fluid inlet port 50 for delivering embryo-containing irrigant fluid to filter insert 14. The preferred inlet port 50 is a conventional upright, tapered, tubular fluid inlet nipple and includes outwardly extending threads 52. The threaded design of inlet port 50 facilitates easy attachment and removal of the inlet conduit. Inlet port 50 is adapted to receive thereover a flexible input conduit (not shown) which may be equipped with a selectively operable flow control clamp (not shown) upstream of the inlet port to control the rate of fluid flow to inlet port 50.

As best illustrated in FIG. 2, the lower end of inlet port 50 is preferably positioned at least slightly below the lower extent of outlet port 22. In this way, incoming irrigant fluid is delivered at a fluid level equal to the minimum existing fluid level in the vessel 12. Accordingly, incoming irrigant fluid is not directed downwardly in an unimpeded fashion for a substantial free-fall distance within the collection device and thus does not cause splashing and subsequent foaming with the existing irrigant fluid contained in the embryo collection device.

In the use of device 10, the lid member 16 is first firmly screwed to filter insert 14 to form a fluid-tight container. Next, the collection device is coupled to an irrigation fluid flow by attaching an input conduit to the upper end of port 50. The collection device is also coupled to a fluid recovery system or a drain by attaching an output conduit to port 22.

In the next step, non-embryo-containing irrigant fluid is conveyed into collection device 10 through inlet port 50. The fluid provides a cushioning entry bath for receiving embryos. Next, embryo-containing irrigant is conveyed into collection device 10. As described previously, such incoming fluid is delivered at a fluid level equal to the existing fluid level in the collection device so that the incoming irrigant fluid does not cause splashing with the existing irrigant fluid.

At this point, the irrigant fluid passes into insert 14 and laterally through filter 26. Such fluid then passes into the region outboard of the filter 26 and ultimately passes from vessel 12 through port 22 for recovery or disposal. The embryos within the fluid are extracted from the irrigant fluid by filter 26 and are allowed to descend into isolation cell area 42. Since filter 26 is positioned below outlet port 22, it remains submerged at all times and embryos attached thereto do not become dehydrated.

Once all of the incoming irrigant fluid has entered the device 10, the input and output conduits are disconnected and plugs 54 and 56 may be inserted into inlet and outlet ports 50 and 22, respectively, to facilitate spill-proof transportation to an examination site. Alternatively, if the collected specimens are to be examined on-site, lid member 16 is removed, and collection device 10 is placed within a conventional microscope for examination, identification and extraction/manipulation of the embryos. This is possible because of the relatively low height of the collection device 10 and the fact that the base 18 and filter insert 14 are at least translucent for passage of light therethrough. Moreover, the construction of the isolation cell ribs 40 serves to focus and concentrate light passing through base 18 and bottom wall 30. The residual fluid within the vessel 12 does not substantially detract from this procedure, particularly in view of the fact that the filter 26 permits red blood cells to pass, thereby leaving a clear, easy to search solution.

The invention as described above provides numerous advantages. For example, the collection device has minimal height to its lower vessel sidewall in order to place the discharge end of the fluid inlet port flush or slightly below the surface of the fluid pool already established in the bottom of the device. This allows the fluid to enter the device with NO splashing and subsequently no foaming. By minimizing vacant dead air space in the device, this design economizes on overall device size which is important when attaching the device to the operator's coveralls, when the device is positioned and rotated during examination on the microscope stage's limited space, and when storing the device between collections.

Additionally, the collection device provides for superior fluid motion stabilization. Fluid motion and subsequent specimen shift inevitably created by the user moving the lower vessel across the microscope stage is eliminated by the buffering action of the collection device's flow-through vertical filter walls. All conventional petri dishes used for searching as well as all patented collection devices (which permit searching in the lower vessel) have solid plastic walls which the fluid motion "waves" bounce off of, thereby prolonging this disruptive wave motion which repeatedly relocates specimens inside the search vessel. Motion waves contacting the present collection device are broken up as they hit the screen and then allowed to pass through into the region outboard of the filter. This eliminates the fluid rebound effect seen in the solid wall dishes and the resultant shift of specimens inside the vessel typically encountered during the embryo search process.

The present invention is also advantageous because it provides for ports which seal closed after collection. Sealibility of the ports is advantageous because it eliminates contamination and accidental dry-out after collection. When more than one donor is collected during a farm visit, frequently the collection filters are not immediately searched after use. The filter is carried to the microscope station and secured in an upright manner until it can be searched 30 minutes or more later. The present invention allows the user to seal off all openings in the device post collection to prohibit contaminants (bacteria, smoke, dust, other liquids, . . . ) from entering the device between the time that collection is completed and searching is initiated.

Sealibility of the ports is also advantageous because it eliminates leakage onto the microscope stage. Fluid in the collection device is completely contained at all times within the search vessel, and can never leak onto the microscope stage.

The present invention also provides for fluid recycling capability. The majority of donors are collected by suspending one liter of phosphate bufferred saline (PBS) above the cow and allowing the fluid to gravity feed into the uterus. Over the course of 20–30 minutes and 8–12 "fills/empties", the liter is run through the uterus, through the filter, and out onto the ground. However, when the technician is presented with a large uterus, or incurs a rupture in the uterine wall mid-flush, he/she would then elect to run additional fluid through the uterus. Unfortunately, this requires stopping to prepare another liter of PBS (plus the cost of another liter with its additives).

Previous attempts to avoid these problems of down time and the inconvenience and cost of preparing additional solution by means of fluid recycling have encountered definite flaws. The present invention is advantageous because it only requires a single user to manipulate 2 pinch clamps. The system starts with a suspended liter of solution which gravity feeds into the uterus, out through the collection device, and into an empty graduated fluid recovery bag attached by conduit tubing to the outflow port. When the suspended bag is empty, the fluid recovery bag (which is now full of PBS) is suspended above and the flush procedure continues as before. If a blood release would occur as outlined above, with the present invention each uterine fill would be with crystal clear PBS out of the suspended bag. This gives the technician the on-going immediate ability to visually measure fluid recovery efficiency by comparing measured fluid in the lower bag with fluid remaining in the bag hanging above the donor.

The present invention also allows the user to flush the tract completely with non-recycled fluid and capture that fluid for later re-use and allows the user to recycle fluid through the uterus when presented with an exceptionally large uterus.

Another advantage of the present invention is its anti-foaming design. To eliminate foaming, the central inlet port of the Biogrid device extends straight down through the lid so that the discharge end of the port is slightly below the fluid surface level in the lower half of the device. This positioning results in no fluid splash and therefore no foaming. Fluid enters the center of the existing fluid pool as an unbroken, continuous fluid path and is dispersed immediately and evenly in all directions towards the filtering sidewalls.

Another unique feature of the vertical inlet port is that it eliminates the possibility for embryos to remain isolated and concealed inside the discharge tube. This likelihood increases as the slope deviates away from vertical.

The collection lid of the present invention is advantageous because it attaches to the base vessel in a threaded clockwise motion. The two parts are screwed together and therefore securely locked in a watertight seal throughout the entire collection procedure. This closure method is unique and superior to all prior art. The lid will not open prematurely or unexpectedly. In addition, the lid has two accessory holes whereby a lanyard (with clip) would allow the technician to attach the filter device to the cow's haircoat, around a convenient bar on the squeeze chute, or actually attach the filter directly and securely to the breast pocket of the operator's coveralls for a one person operation.

One of the most unique and beneficial features of the collection device is its specimen stabilization architecture which extends up and away from the inside horizontal wall of the insert filter vessel. These stabilization barriers function as isolation cells, and localize specimens thereby prohibiting specimen drift which occurs when the lower vessel is moved across the microscope stage during the search process. This architecture serves to isolate and retain the embryo in the specific cell that it comes to rest in. The specimen cannot roll out of or away from the cell that it falls into. Presuming the entire bottom wall of the lower vessel is searched, all embryos will be located after only one pass through the dish. Additionally, each isolation cell in the dish has a unique sequential number etched into the horizontal cell wall. Accordingly, when the user returns the dish to the microscope, he knows which cell to start searching in and knows that unlocated specimens have not shifted back into previously searched fields.

The present invention also provides a novel thermal buffer ridge. Embryos are sensitive to temperature extremes and will be damaged or killed if they are unknowingly exposed to these extremes for prolonged periods. This situation occurs most often on the microscope stage. Some scope stages tend to heat up after prolonged use (heat from the illuminator), which is an especially real concern when working during the summer in a hot barn. The opposite harmful effect occurs in the winter when a petri dish is placed on a ice-cold stage, or when prolonged searching is conducted in a cold barn or milkroom.

To prevent the possibility of embryo damage due to extreme temperature shock, the present invention features a circular thermal vent ridge underneath the horizontal bottom wall of the lower vessel. The ridge maintains a neutral vented dead-air space between the stage and the device, thus preventing the direct transfer of damaging extreme hot or cold temperatures into the lower vessel while searching. None of the prior art features this thermal safety ridge.

I claim:

1. An embryo collection device for extracting and holding embryos from an embryo-containing irrigant fluid, comprising:

a vessel including a base and a sidewall, said sidewall including structure defining an outlet port spaced a distance above said base for conveying filtered irrigant fluid from said vessel;

filter means within said vessel for filtering embryos from the embryo-containing fluid, said filter means including an upright irrigant fluid-pervious filter spaced inwardly from said sidewall and presenting inner and outer opposed faces and an upper margin, there being an irrigant fluid-retaining region between said outer face of said upright filter and said vessel sidewall; and a lid member removably attached to said filter means and including structure defining an irrigant fluid inlet therethrough for delivering embryo-containing irrigant fluid to said filter means, said vessel sidewall port being located relative to the upper margin of said filter for continuously maintaining substantially the entirety of said upright filter and both said inner and outer faces thereof in contact with said irrigant fluid during and subsequent to filtration of the fluid, said irrigant fluid being maintained within said region and inboard of said filter whereby embryos that may become attached to said filter during filtration remain bathed within irrigant fluid during and subsequent to filtration of the fluid.

2. An embryo collection device for extracting and holding embryos from an embryo-containing irrigant fluid, comprising:

a vessel including a base and a sidewall, said sidewall including structure defining an outlet port spaced a distance above said base for conveying filtered irrigant fluid from said vessel;

filter means within said vessel for filtering embryos from the embryo-containing fluid, said filter means including an upright irrigant fluid-pervious filter spaced inwardly from said sidewall and presenting inner and outer opposed faces and an upper margin, there being an irrigant fluid-retaining region between said said outer face of said upright filter and said vessel sidewall; and a lid member removably attached to said filter means and including structure defining an irrigant fluid inlet therethrough for delivering embryo-containing irrigant fluid to said filter means, said vessel sidewall port being located relative to the upper margin of said filter for continuously maintaining substantially the entirety of said upright filter and both said inner and outer faces thereof in contact with said irrigant fluid during and subsequent to filtration of the fluid, said irrigant fluid being maintained within said region and inboard of said filter whereby filtered embryos remain bathed within irrigant fluid during and subsequent to filtration of the fluid, said vessel base being substantially flat for permitting placement of the device in a microscope for embryo identification and counting.

3. An embryo collection device for extracting and holding embryos from an embryo-containing irrigant fluid, comprising:

a vessel including a base and a sidewall, said sidewall including structure defining an outlet port spaced a distance above said base for conveying filtered irrigant fluid from said vessel;

filter means within said vessel for filtering embryos from the embryo-containing fluid, said filter means including an upright irrigant fluid-pervious filter spaced inwardly from said sidewall and presenting inner and outer opposed faces and an upper margin, there being an irrigant fluid-retaining region between said outer face of said upright filter and said vessel sidewall; and a lid member removably attached to said filter means and including structure defining an irrigant fluid inlet therethrough for delivering embryo-containing irrigant fluid to said filter means, said vessel sidewall port being located relative to the upper margin of said filter for continuously maintaining substantially the entirety of said upright filter and both said inner and outer faces thereof in contact with said irrigant fluid during and subsequent to filtration of the fluid, said irrigant fluid being maintained within said region and inboard of said filter whereby filtered embryos remain bathed within irrigant fluid during and subsequent to filtration of the fluid, said vessel base and sidewall being formed of substantially transparent synthetic resin material.

4. An embryo collection device for extracting and holding embryos from an embryo-containing irrigant fluid, comprising:

a vessel including a base and a sidewall, said sidewall including structure defining an outlet port spaced a distance above said base for conveying filtered irrigant fluid from said vessel;

filter means within said vessel for filtering embryos from the embryo-containing fluid, said filter means including an upright filter spaced inwardly from said sidewall and presenting an upper margin, there being an irrigant fluid-retaining region between said upright filter and said vessel sidewall; and a lid member removably attached to said filter means and including structure defining an irrigant fluid inlet therethrough for delivering embryo-containing irrigant fluid to said filter means, said vessel sidewall port being located relative to the upper margin of said filter for continuously maintaining substantially the entirety of said upright filter in contact with said irrigant fluid during and subsequent to filtration of the fluid, said irrigant fluid being maintained within said region and inboard of said filter whereby filtered embryos remain bathed within irrigant fluid during and subsequent to filtration of the fluid, said filter means further including support structure for said upright filter, and including structure for directing incoming embryo-containing irrigant fluid thereto, said support structure including a bottom wall bonded to said vessel base, a plurality of upwardly extending posts integrally molded to said bottom wall, and a connector bonded to the top of said support posts and extending upwardly therefrom.

5. The collection device of claim 4, said support structure configured for supporting said upright filter in a semi-sealing relationship with said vessel, wherein the bottom edge of said upright filter engages said bottom wall and the upper margin of said filter engages said support structure connector so that embryo-containing irrigant fluid delivered to said filter means is filtered by said upright filter and the filtered irrigant fluid is delivered to said region between said upright filter and said outer housing sidewall, with excess amounts of said irrigant fluid passing out of said vessel through said port.

6. The collection device of claim 5, said bottom wall including a plurality of upwardly extending, intersecting ribs defining isolation cells inboard of said upright filter bottom edge for facilitating isolation and localization of embryos filtered from said irrigant fluid.

7. The collection device of claim 5, said connector including threads integrally molded to a surface thereof for threadably engaging said lid member.

8. The collection device of claim 6, said connector including an outwardly extending horizontal ridge integrally molded above said sidewall for engaging the top of said outer housing sidewall.

9. An embryo collection device for extracting and holding embryos from an embryo-containing irrigant fluid, comprising:

a vessel including a base and a sidewall and defining a fluid retention vessel for retaining filtered irrigant fluid therein, said sidewall including structure defining an outlet port spaced a distance above said base for conveying filtered irrigant fluid which rises to the level of said outlet port out of said outer housing, and for maintaining within said outer housing a minimum level of irrigant fluid;

filter means within said vessel for filtering embryos from the embryo-containing fluid;

means for delivery of embryo-containing irrigant fluid to said filter means including an irrigant fluid inlet nipple presenting a fluid inlet end and a fluid outlet end, said nipple outlet end being located at a level at least slightly below said outlet port for delivery of said embryo-containing irrigant fluid below said minimum level in order to avoid splashing of the fluid in said outer housing.

10. The collection device of claim 9, said filter means including an upright filter presenting an upper margin, said outer housing sidewall port being located relative to the upper margin of said filter for continuously maintaining substantially the entirety of said upright filter in contact with said irrigant fluid during and subsequent to filtration of the fluid.

11. In a method of collecting and identifying embryos from an embryo-containing irrigant fluid, said method including the steps of passing said fluid through a vessel equipped with an upright irrigant fluid-pervious filter presenting inner and outer opposed faces, causing said embryo-containing irrigant fluid to pass laterally through said upright filter and collecting said embryos within said vessel on one side of said upright filter, the improvement which comprises the step of continuously maintaining substantially the entirety of said upright filter and both said inner and outer faces thereof in contact with said irrigant fluid both during and subsequent to filtration of the embryo-containing irrigant fluid so that embryos that may become attached to said filter during filtration remain bathed within irrigant fluid during and subsequent to filtration of the embryo-containing fluid.

12. In an embryo collection device for extracting and holding embryos from an embryo-containing irrigant fluid, said device including a vessel presenting a base, an upstanding sidewall and an upright filter in the vessel for filtering of embryos within said irrigant fluid, the improvement which comprises structure for maintaining a minimum level of irrigant fluid within said vessel both during and subsequent to filtration of said irrigant fluid, including an irrigant fluid outlet port on said sidewall above said base and an irrigant fluid delivery inlet nipple presenting an inlet end and an outlet end, said outlet end being disposed at least slightly below said outlet port for delivery of incoming irrigant fluid to said chamber with a minimum of splashing of the fluid.

* * * * *